United States Patent [19]
Burrows

[11] Patent Number: 5,993,480
[45] Date of Patent: Nov. 30, 1999

[54] MICROWAVABLE HEATING PAD WITH HEAT ACTIVATED FRAGRANCE

[76] Inventor: Christina Burrows, 33 Artist Lake Dr., Middle Island, N.Y. 11953

[21] Appl. No.: 08/782,331

[22] Filed: Jan. 13, 1997

[51] Int. Cl.$^6$ .................................................. A61F 7/00
[52] U.S. Cl. ........................................ 607/114; 607/112
[58] Field of Search ........................... 607/104, 108–112, 607/114; 165/46; 126/204; 62/4

[56] References Cited

U.S. PATENT DOCUMENTS

| | | |
|---|---|---|
| 4,983,798 | 1/1991 | Eckler . |
| 5,020,711 | 6/1991 | Kelley ................................. 607/114 X |
| 5,484,366 | 1/1996 | Wilkinson ........................... 607/114 X |
| 5,496,358 | 3/1996 | Rosenwald .......................... 607/114 X |

*Primary Examiner*—Jeffrey R. Jastrzab
*Assistant Examiner*—Ryan Carter

[57] ABSTRACT

A microwavable heating pad that includes a pouch, accessing apparatus, a sealed bag, and discrete particles. The pouch contains a chamber and has a heat exchange layer contactable with a part of a body to which heat is to be applied. The accessing apparatus is associated with the pouch and is used to selectively access the chamber in the pouch. The sealed bag is replaceably contained in the chamber in the pouch and is accessible through the accessing apparatus and is in heat exchange communication with the heat exchange layer of the pouch. The discrete particles are contained in the sealed bag and are in heat exchange communication therewith and comprise an organic material that is solid at room temperature and exhibits a mesocrystalline transition temperature when subjected to microwave radiation, so that when the sealed bag is subjected to microwave radiation, the discrete particles contained therein exhibit the mesocrystalline transition temperature and generate heat which in turn causes the sealed bag to heat and form a heated sealed bag which is then replaceably inserted into the chamber in the pouch through the accessing apparatus with the pouch then being contacted to the part of the body to which the heat is to be applied until the heat becomes exhausted at which time the sealed bag is removed from the pouch through the accessing apparatus.

32 Claims, 2 Drawing Sheets

«5,993,480»

MICROWAVABLE HEATING PAD WITH HEAT ACTIVATED FRAGRANCE

BACKGROUND OF THE INVENTION

1. Field of the Invention

The present invention relates to a heating pad. More particularly, the present invention relates to a microwavable heating pad with heat activated fragrance.

2. Description of the Prior Art

It has been found that many medical problems which effect individuals can be successfully treated by applying heat to the effected area. Although a variety of devices have been created for use by individuals to provide heat to a particular area of the body, no system has been achieved which is capable of providing reliable, controlled, and repeatable delivery of a precise temperature level in an easily used and convenient form.

The use of heat therapy for many transitory problems, such as pains, muscle pulls, etc. has been practiced for many years. Typically, these maladies are treated with electrically heated pads, hot towels, and/or hot compresses. Additionally, these maladies can be treated with ointments whose smells can be quite objectionable, especially when heat is applied thereto.

Numerous innovations for warming devices and deodorants have been provided in the prior art that will be described. Even though these innovations may be suitable for the specific individual purposes to which they address, however, they differ from the present invention in that they do not teach a microwavable heating pad with heat activated fragrance.

FOR EXAMPLE, U.S. Pat. No. 4,367,203 to Landsberger teaches a thermal sensitive deodorant wafer utilized to neutralize odors caused by subjecting certain materials to elevated temperatures. A pad is impregnated with a heat releasible deodorant and is encapsulated in a thermal sensitive shell to form a wafer-like element. The shell decomposes when subjected to the elevated temperatures whereupon the deodorant is released to neutralize the odors.

ANOTHER EXAMPLE, U.S. Pat. No. 4,931,608 to Bills teaches a hot pad for absorbing energy in a microwave oven and for heating articles in thermally conductive contact therewith. The pad includes a flexible and conformable pad defining a plurality of individual flexible and conformable closed pockets. Each of the pockets is formed of a microwave-transmissive heat resistant material and at least partially filled with microwave absorbing particulate matter. The microwave-heated hot pad is used by being disposed in thermally conductive contact with an essentially microwave-transmissive article to be heated, e.g. non-comestible.

STILL ANOTHER EXAMPLE, U.S. Pat. No. 4,914,717 to Gibbon teaches a device and method for treating a localized area of pain in the human body by the application of a heating pad to the localized area. The heating pad includes a layer of matrix material which is actuable by exposure to microwave energy. The heating pad is heated by exposure to microwave energy to a temperature above ambient prior to application to the localized area. The microwavable layer is sandwiched between upper and lower elastomeric layers formed from materials which are non-absorptive of microwave energy.

YET ANOTHER EXAMPLE, U.S. Pat. No. 4,983,798 to Eckler et al. teaches warming devices having solid organic particulates that are solid at room temperature and which exhibit a mesocrystalline transition temperature within a range of about 30° to about 200° C. The particles can be heated by a variety of methods, such as microwave radiation or hot liquids. Contemplated objects include vacuum bottles, coffee mugs, stadium pads, foot warming boxes, mittens, caps, snowsuits, and other wearing apparel. The solid particles act as a reusable heat reservoir to release heat over an extended period of time or absorb ambient heat and serve a protective function.

STILL YET ANOTHER EXAMPLE, U.S. Pat. No. 5,164,178 to Muysson teaches a solid granular deodorant that consists of a porous granular $CaSo_4 2H_2O$ base, a portion of essential oils adsorbed on the porous granular base and microcapsules filled with another portion of the essential oils. The portion of the essential oils absorbed on the granular base is present in an amount of from 2% to 18% by weight and the other portion of the essential oils in the microcapsules is present in an amount for from 0.5% to 4% by weight. The microcapsules are breakable by impacts, crushing, or heating. The granular deodorant is packed in a sealed pouch which has micro-holes on one side covered by a removable and repositionable adhesive tape.

FINALLY, YET STILL ANOTHER EXAMPLE, U.S. Pat. No. 5,534,021 to Dvoretzky et al. teaches a delivery system that includes a carrier constructed for securely retaining a heat generating pad while also being able to be easily and securely mounted to the skin surface of an individual for providing heat therapy to any desired site or location. The heat generating pad is securely retained using either permanent or separable fastening means. By employing separable fastening means, the same carrier can be repeatedly employed by changing to a new heat generating pad after the previously used pad is exhausted. In addition, the carrier incorporates either adhesive means for mounting the carrier and pad to a user or employs a separable fastening means mounted to the carrier to enable the carrier and pad to be easily positioned, wherever desired, and securely retained in that position by engaging the fastening means.

It is apparent that numerous innovations for warming devices and deodorants have been provided in the prior art that are adapted to be used. Furthermore, even though these innovations may be suitable for the specific individual purposes to which they address, however, they would not be suitable for the purposes of the present invention as heretofore described.

SUMMARY OF THE INVENTION

ACCORDINGLY, AN OBJECT of the present invention is to provide a microwavable heating pad with heat activated fragrance that avoids the disadvantages of the prior art.

ANOTHER OBJECT of the present invention is to provide a microwavable heating pad with heat activated fragrance that is simple and inexpensive to manufacture.

STILL ANOTHER OBJECT of the present invention is to provide a microwavable heating pad with heat activated fragrance that is simple to use.

BRIEFLY STATED, YET ANOTHER OBJECT of the present invention is to provide a microwavable heating pad that includes a pouch, accessing apparatus, a sealed bag, and discrete particles. The pouch contains a chamber and has a heat exchange layer contactable with a part of a body to which heat is to be applied. The accessing apparatus is associated with the pouch and is used to selectively access the chamber in the pouch. The sealed bag is replaceably contained in the chamber in the pouch and is accessible through the accessing apparatus and is in heat exchange communication with the heat exchange layer of the pouch. The discrete particles are contained in the sealed bag and are in heat exchange communication therewith and comprise an organic material that is solid at room temperature and exhibits a mesocrystalline transition temperature when subjected to microwave radiation, so that when the sealed bag is subjected to microwave radiation, the discrete particles contained therein exhibit the mesocrystalline transition temperature and generate heat which in turn causes the sealed bag to heat and form a heated sealed bag which is then replaceably inserted into the chamber in the pouch through the accessing apparatus with the pouch then being contacted to the part of the body to which the heat is to be applied until the heat becomes exhausted at which time the sealed bag is removed from the pouch through the accessing apparatus.

The novel features which are considered characteristic of the present invention are set forth in the appended claims. The invention itself, however, both as to its construction and its method of operation, together with additional objects and advantages thereof, will be best understood from the following description of the specific embodiment when read and understood in connection with the accompanying drawing.

BRIEF DESCRIPTION OF THE DRAWING

The figures of the drawing are briefly described as follows.

Figure 1:
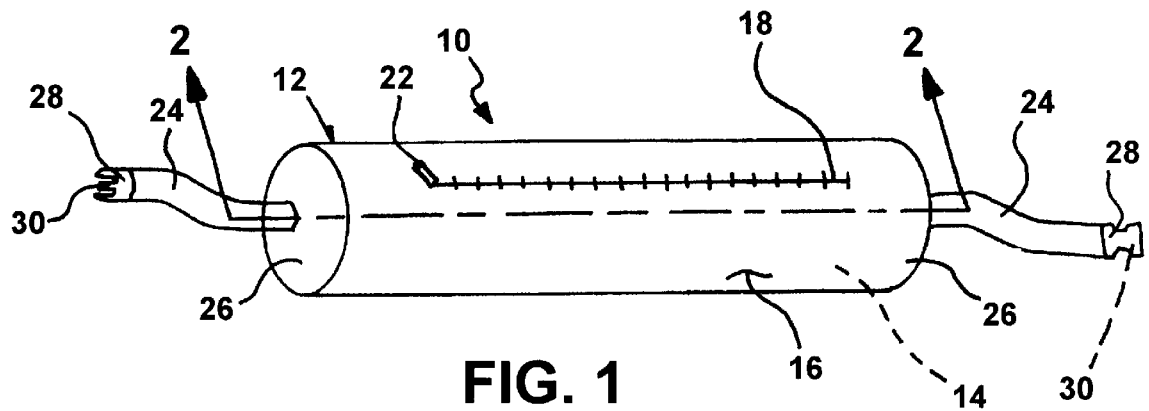
FIG. 1 is a diagrammatic perspective view of the present invention with hook and loop fasteners VELCRO® being utilized to fastening the present invention around the desired site.

LIST OF REFERENCE NUMERALS UTILIZED IN THE DRAWING 10 microwavable heating pad with heat activated fragrance of the present invention
12 pouch
14 chamber
16 heat exchange layer
18 opening
22 zipper
24 pair of elongated straps
26 pair of opposing ends
28 free end
30 hook and loop fasteners
32 buckle
34 sealed bag
36 discrete particles
38 strongly absorbent solid granular porous base
40 microcapsules
42 resealable storage bag

DETAILED DESCRIPTION OF THE PREFERRED EMBODIMENT

Referring now to the figures and particularly to FIG. 1, the microwavable heating pad with heat activated fragrance of the present invention is shown generally at 10.

The microwavable heating pad with heat activated fragrance 10 includes a pouch 12 that contains a chamber 14 and has a heat exchange layer 16 with a surface temperature. The heat exchange layer 16 of the pouch 12 is contactable with a part of a body to which heat is to be applied.

The pouch 12 may be constructed of virtually any material which can withstand the actuating method and heated particle temperature. Preferably, the pouch 12 is suitably constructed to release retained heat in a controlled manner over about 1 to about 6 hours at temperatures of about 35° to about 70° C.

The pouch 12 includes radiation barriers on all its surfaces, such as natural or synthetic fiber, to direct heat towards the part of the body to which the heat is to be applied.

In addition, the exterior surfaces of the pouch 12 which contact the user, i.e. the "contact layer", may be made of a temperature regulator material which tempers the released heat to provide a comfortable contact temperature in the range of 35° to 100° C. Suitable regulating materials include cotton, polyester, and/or wool in the form of mats or a plurality of cloth layers.

The pouch 12 further has an opening 18 therealong that provides access to the chamber 14 in the pouch 12 and which is selectively closed by a zipper 22.

The microwavable heating pad with heat activated fragrance 10 further includes a pair of elongated straps 24, each of which extends outwardly from an end of a pair of opposing ends 26 of the pouch 12 and has free ends 28.

The microwavable heating pad with heat activated fragrance 10 further includes hook and loop fasteners 30 that selectively fasten the free ends 28 of the pair of elongated straps 24 to each other around the part of the body to which the heat is to be applied.

Figure 1A:
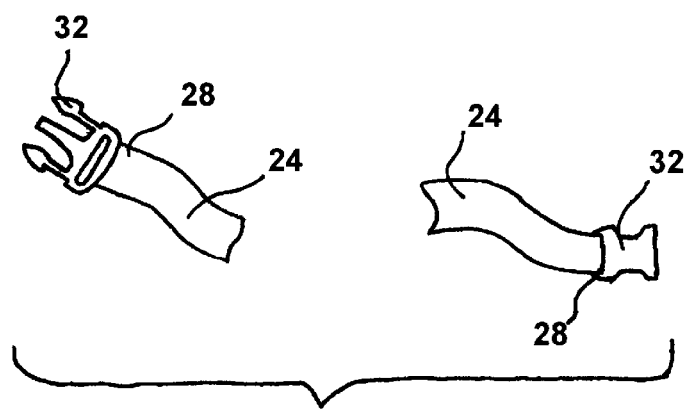
FIG. 1A is diagrammatic perspective view of buckle portions utilized for fastening the present invention around the desired site as an alternative to the hook and loop fasteners VELCRO® shown in FIG. 1.

As shown in FIG. 1A, alternatively, a buckle 32 can be employed to selectively fasten the free ends 28 of the pair of elongated straps 24 to each other around the part of the body to which the heat is to be applied.

Figure 2:
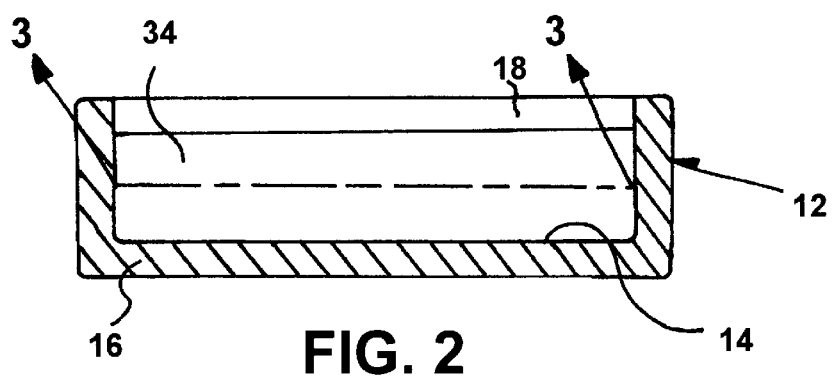
FIG. 2 is an enlarged cross sectional view taken on line 2—2 in FIG. 1 illustrating the internally contained sealed microwavable heating bag.

As shown in FIG. 2, the microwavable heating pad with heat activated fragrance 10 further includes a sealed bag 34 that is replaceably contained in the chamber 14 in the pouch 12 and is accessible through the opening 18 and further is in heat exchange communication with the heat exchange layer 16 of the pouch 12.

Figure 3:
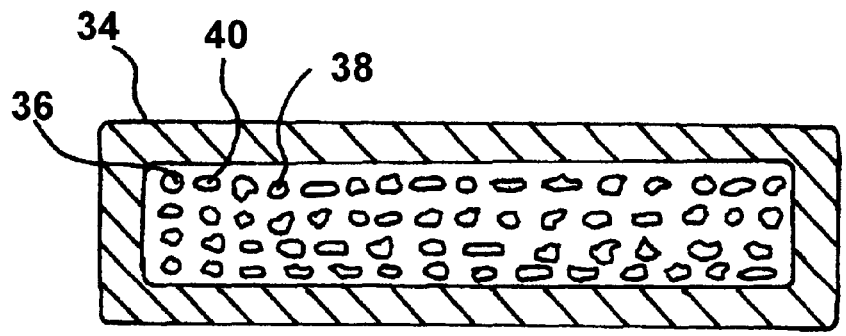
FIG. 3 is a cross sectional view taken on line 3—3 in FIG. 2 illustrating the contents of the internally contained sealed microwavable heating bag.

As shown in FIG. 3, the microwavable heating pad with heat activated fragrance 10 further includes discrete particles 36 that are contained in the sealed bag 34 and are in heat exchange communication therewith. The discrete particles 36 are organic and solid at room temperature and exhibit a mesocrystalline transition temperature when subjected to microwave radiation. The discrete particles 36 are characterized by a mesocrystalline phase transition temperature within a range from about 30° C. to about 200° C., and preferably within a range from about 35° C. to about 100° C., since the heat exchange layer 16 of the pouch 12 is contactable with the part of the body to which heat is to be applied.

The mesocrystalline phase of the discrete particles 36 represents a solid transition state before melting. The transition temperature is detected by the transition exotherm from conventional differential thermal analysis. See Murill et al., "Solid Phase transition as Determined by Differential Scanning Calorimetry," Thermochin Acta., 3 (1970) pp. 311–315. The detected solid phase change reversibility stores and releases enthalpy within the crystal structure. It is this energy reservoir which the present invention uses as a dynamic source of heat.

TABLE 1 lists a plurality of organic particulates which exhibit a mesocrystalline phase change when heated. Other suitable materials readily may be designated by routine differential thermal analysis tests as mentioned, supra. Many of the listed organic particulates are polyols which represent a preferred class of materials. Most preferred among the polyols are trimethylolethane, pentaerythritol, neopentylglycol, and mixtures thereof. Trimethylolethane is especially preferred because it has very low toxicity and is commercially available.

TABLE 1

| MATERIAL | Transition Temperature (° C.) |
|---|---|
| Neopentylglycol | 40–43 |
| Monofluoropentaerythritol | 68–72 |
| Hexachloroethane | About 71 |
| Diaminopentaerythritol | 68–73 |
| $(CH_3)_2C(CN)$—$(CH_3)_2(CN)$ | 71–73 |
| $(CH_3)_2C(Cl)$—$(CH_3)_2(Cl)$ | 75–100 |
| Monoaminopentaerythritol | 86–91 |
| Trimethylolethane | About 81 |
| 2-amino-2-methyl-1,3-propanediol | 79–80 |
| 2-hydroxymethyl-2-nitro-1,3-propanediol | 79–80 |
| $(CH_3)_2C(CO_2H)$—$(CH_3)_2(CH_2OH)$ | 108–111 |
| Tris(hydroxymethyl) acetic acid | 124–127 |
| 2-amino-2-hydroxymethyl-1,3-propanediol | 131–134 |
| Dimethylpropionic acid | 152–155 |
| Pentaerythritol | 181–183 |

Heat energy is introduced to the discrete particles 36 by subjecting the sealed bag 34 to microwave radiation. For example, the sealed bag 34 having about 120 gms. of trimethylolethzine can be irradiated for about 5 minutes in a microwave oven of 160 watts to induce a mesocrystalline phase change.

For convenience, the term "particles" is used herein to describe crystals, aggregates, spheres, pellets, and all other particulate shapes.

A particulate form is advantageous because compartments containing solids are easier to seal than compartments holding either liquids or gases. Organic materials that remain solid throughout the heating represent a preferred form of the present invention, however, nothing prevents the use of a seal or sealing means which is sufficient to contain some quantity of melted material. Suitable sealing means includes liquid tight apparatus connections and encapsulation materials for the organic particulates. Exemplary encapsulation materials are thermoset plastics, such as urea-formaldehyde, epoxies, and phenolic resins.

The microwavable heating pad with heat activated fragrance 10 further includes a fragrance that is contained in the sealed bag 34 and is permeable therethrough and intermixed with the discrete particles 36.

As also shown in FIG. 3, the fragrance consists of a strongly absorbent solid granular porous base 38 that is impregnated with essential oils, and by microcapsules 40 that also contain essential oils with the same fragrance.

The strongly absorbent solid granular porous base 38 is either silica, alumina, or other metallic oxides, but preferably is CaSo42H2O, and departs a neutral color from the essential oils.

The essential oil-filled microcapsules 40 consist of a thin vegetable substance layer which is broken as a consequence of heating and thereby instantaneously releases the fragrance which they contain.

As a result, the instantaneous release of the microencapsulated fragrance is added to the normal release of the fragrance which is absorbed on the strongly absorbent solid granular porous base 38 and thereby increasing the overall fragrance effect.

The concentration of the essential oils absorbed on the strongly absorbent solid granular porous base 38 and in the essential oil-filled microcapsules 40 range, respectively, between 2% to 18% and 0.5% to 4% by weight, and are preferably 13% and 2% by weight, respectively.

During manufacture, in order to differentiate the various product fragrances, speckles made of plastic material, preferably polyester, and of different corresponding colors are mixed with the strongly absorbent solid granular porous base 38 and the essential oil-filled microcapsules 40 in an amount between 1% and 5% by weight, and preferably 2% by weight.

The fragrance thus obtained provides a two-fold fragrance action. First the regular action related to the perfume release from the strongly absorbent solid granular porous base 38, and second, the instantaneous action when the essential oil-filled microcapsules 40 are broken following heating.

Figure 4:
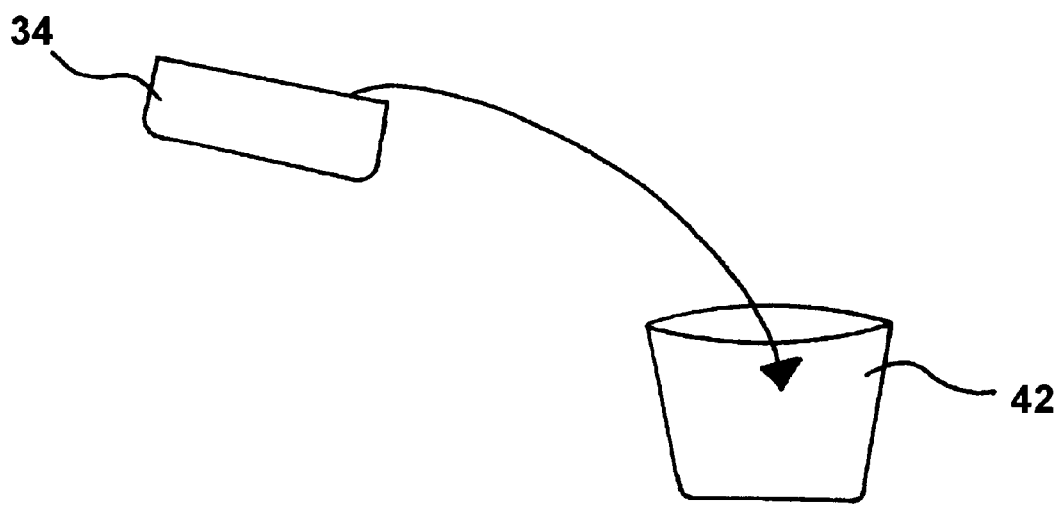
FIG. 4 is a diagrammatic perspective view illustrating the internally contained sealed microwavable heating bag being placed in a sealed storage bag after use.

As shown in FIG. 4, the microwavable heating pad with heat activated fragrance 10 further includes a resealable storage bag 42 that replaceably receives the sealed bag 34 after removal from the pouch 12 and awaiting the next use so as to ensnare any previously released fragrance.

It will be understood that each of the elements described above, or two or more together, may also find a useful application in other types of constructions differing from the types described above.

While the invention has been illustrated and described as embodied in a microwavable heating pad with heat activated fragrance, it is not limited to the details shown, since it will be understood that various omissions, modifications, substitutions and changes in the forms and details of the device illustrated and its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute characteristics of the generic or specific aspects of this invention.

The invention claimed is:

1. A microwavable heating pad, comprising:
  a) a pouch containing a chamber and having a heat exchange layer with a surface temperature; said heat exchange layer of said pouch being contactable with a part of a body to which heat is to be applied;
  b) accessing means associated with said pouch and being urged for selectively accessing said chamber in said pouch;
  c) a sealed bag replaceably contained in said chamber in said pouch and accessible through said accessing means; said sealed bag being in heat exchange communication with said heat exchange layer of said pouch;
  d) discrete particles contained in said sealed bag and being in heat exchange communication therewith; said discrete particles comprising an organic material being solid at room temperature and exhibiting a mesocrystalline transition temperature when subjected to microwave radiation, so that when said sealed bag is subjected to microwave radiation, said discrete particles contained therein exhibit said mesocrystalline transition temperature and generate heat which in turn causes said sealed bag to heat and form a heated sealed bag; and e) a fragrance contained in said sealed bag.

2. The pad as defined in claim 1, wherein said accessing means includes an opening in said pouch that is selectively closed by a zipper.

3. The pad as defined in claim 1, wherein said discrete particles comprise a polyol.

4. The pad as defined in claim 3, wherein said polyol is selected from the group consisting of trimethylolethane, pentaerythritol, and neopentylglycol.

5. The pad as defined in claim 4, wherein said polyol is trimethylolethane.

6. The pad as defined in claim 1, wherein said mesocrystalline transition temperature is within a range from about 30° to about 200° C.

7. The pad as defined in claim 6, wherein said mesocrystalline transition temperature is within a range from about 35° to about 100° C.

8. The pad as defined in claim 1; further comprising regulating means for regulating said surface temperature of said heat exchange layer of said pouch.

9. The pad as defined in claim 8, wherein said regulating means includes a material selected from the group consisting of cotton, polyester, and wool.

10. The pad as defined in claim 8, wherein said regulating means includes a form selected from the group consisting of mats and a plurality of cloth layers.

11. The pad as defined in claim 8, wherein said regulating means regulates said surface temperature of said heat exchange layer of said pouch within a range from about 35° to about 70° C.

12. The pad as defined in claim 1; further comprising maintaining means for selectively maintaining said pouch to the part of the body to which the heat is to be applied.

13. The pad as defined in claim 12, wherein said maintaining means includes a pair of elongated straps, each of which extends outwardly from an end of a pair of opposing ends of said pouch and has a free end.

14. The pad as defined in claim 13, wherein said maintaining means further includes fastening means for selectively fastening said free ends of said elongated straps of said maintaining means to each other around the part of the body to which the heat is to be applied; said fastening means of said maintaining means is disposed at said free ends of said elongated straps of said maintaining means.

15. The pad as defined in claim 14, wherein said fastening means of said maintaining means includes hook and loop fasteners.

16. The pad as defined in claim 14, wherein said fastening means of said maintaining means includes a buckle.

17. The pad as defined in claim 1, wherein said fragrance is a solid granular fragrance consisting of:

a) a porous granular base;

b) a portion of essential oils adsorbed on said porous granular base; and c) microcapsules filled with another portion of said essential oils; said microcapsules being breakable by heating, so that when said sealed bag is subjected to the microwave radiation, said microcapsules break and release said fragrance.

18. The pad as defined in claim 17, wherein said porous granular base is a metallic oxide.

19. The pad as defined in claim 18, wherein said metallic oxide is selected from the group consisting of silica and alumina.

20. The pad as defined in claim 18, wherein said porous granular base consists of $CaSo_4 2H_2O$ particles.

21. The pad as defined in claim 17, wherein said portion of said essential oils adsorbed on said porous granular base is present in an amount of from 2% to 18% by weight.

22. The pad as defined in claim 21, wherein said portion of said essential oils adsorbed on said porous granular base is present in an amount of 13% by weight.

23. The pad as defined in claim 17, wherein said another portion of said essential oils in said microcapsules is present in an amount of from 0.5% to 4% by weight.

24. The pad as defined in claim 23, wherein said another portion of said essential oils in said microcapsules is present in an amount of 2% by weight.

25. The pad as defined in claim 17, wherein said microcapsules consist of a thin vegetable substance layer.

26. The pad as defined in claim 17, further comprising a plurality of colored plastic speckles having a predetermined color and being mixed with said porous granular base and said microcapsules; said predetermined color of said plurality of colored plastic speckles being chosen to indicate said fragrance.

27. The pad as defined in claim 26, wherein said plurality of colored plastic speckles are polyester.

28. The pad as defined in claim 26, wherein plurality of colored plastic speckles are present in an amount from 1% to 5% by weight.

29. The pad as defined in claim 28, wherein said plurality of colored plastic speckles are present in an amount of 2% by weight.

30. The pad as defined in claim 1; further comprising a radiation barrier disposed on said heat exchange layer of said pouch for directing the heat towards the part of the body to which the heat is to be applied.

31. The pad as defined in claim 30, wherein said radiation barrier is selected from the group consisting of natural fiber and synthetic fiber.

32. The pad as defined in claim 1; further comprising a resealable storage bag that replaceably receives said sealed bag after removal from said pouch.

* * * * *